United States Patent [19]

Rule et al.

[11] Patent Number: 4,795,737
[45] Date of Patent: Jan. 3, 1989

[54] PROCESS FOR THE IODINATION OF AROMATIC COMPOUNDS OVER SOLID CATALYSTS

[75] Inventors: Mark Rule; Gerald C. Tustin, both of Kingsport, Tenn.

[73] Assignee: Eastman Kodak Company, Rochester, N.Y.

[21] Appl. No.: 29,959

[22] Filed: Mar. 25, 1987

[51] Int. Cl.$^4$ .............................................. C07C 17/15
[52] U.S. Cl. .................................. 570/203; 570/206; 570/208
[58] Field of Search ............... 570/206, 208, 203, 204

[56] References Cited

U.S. PATENT DOCUMENTS

| | | | |
|---|---|---|---|
| 3,363,010 | 1/1968 | Schwarzenbek | 570/203 |
| 3,600,331 | 8/1971 | Ingwalson | 570/203 |
| 3,644,542 | 2/1972 | Prahl et al. | 570/203 |
| 4,240,987 | 12/1980 | Martin et al. | 570/206 |
| 4,381,785 | 7/1983 | Rosinski et al. | 502/77 |
| 4,513,092 | 4/1985 | Chu et al. | 502/77 |

FOREIGN PATENT DOCUMENTS

| | | | |
|---|---|---|---|
| 0181790 | 5/1986 | European Pat. Off. | 570/206 |
| 77631 | 5/1982 | Japan | 570/206 |
| 159496 | 12/1963 | U.S.S.R. | 570/206 |

OTHER PUBLICATIONS

Groggin, "Unit Processes in Organic Chemistry", Fifth ed, McGraw-Hill Book Co., Inc. p. 262.
Advanced Organic Chemistry: Reactions, Mechanisms, and Structure Mar., McGraw-Hill, 1968, p. 405.
J. Org. Chem. vol. 35, No. 10, 1970, Baird et al, Halogenation with Copper (II) Halides. The Synthesis of Aryl Iodides.
Institute of Catalysis, Siberian Branch of the Academy of Sciences of the USSR, vol. 23, No. 4, pp. 992–994, Jul.–Aug., 1982; Gorodetskaya et al, Oxidative Bromination of Aromatic Compounds . . . .

*Primary Examiner*—Werren B. Lone
*Attorney, Agent, or Firm*—Charles R. Martin; William P. Heath, Jr.

[57] ABSTRACT

Disclosed is a process for iodinating aromatic compounds by reacting an aromatic compound with oxygen in the presence of a catalyst containing alkaline or alkaline earth cations.

13 Claims, No Drawings

PROCESS FOR THE IODINATION OF AROMATIC COMPOUNDS OVER SOLID CATALYSTS

BACKGROUND OF THE INVENTION

1. Field of the Invention

The present invention relates to processes for iodinating aromatic compounds. In particular, a process for iodinating benzene is described. A second process for iodinating naphthalene and other condensed ring aromatics is also described. The processes utilize oxidative iodination over nonzeolitic catalysts containing alkaline and alkaline earth cations.

2. Background of the Invention

It has long been desired to be able to derivatize aromatic compounds and in particular condensed ring aromatic compounds in commercially attractive quantities since many of these compounds possess properties which would fill long sought needs. In particular, the compound 2.6-naphthalene dicarboxylic acid or its esters is particularly desired for use in the manufacture of polyesters which would have excellent barrier properties when fabricated into films, bottles or coatings. However, known techniques for producing 2.6-naphthalene dicarboxylic acid and esters are very expensive and impractical for commercial exploitation.

3. Description of the Prior Art

Synthesis of iodobenzene starting from benzene and iodine is usually carried out in the liquid phase in the presence of an axidative agent, preferably nitric acid. Such techniques have been described in the literature and in particular in Japanese No. 58/77830, U.S.S.R. Pat. No. 453392 and by Datta and Chatterjee in the *Journal of the American Chemical Society*, 39, 437, (1917). Other oxidative agents have also been suggested but none of these have proven to be more efficient or convenient than nitric acid. Typical of the other oxidative agents which have been suffested are iodic acid, sulfur trioxide and hydrogen perioxide as described by Butler in the *Journal of Chemical Education*, 48, 508, (1971). The use of metal halogenides to catalyze iodination has been suggested by Uemura. Noe. and Okano in the *Bulletin of Chemical Society of Japan*, 47, 147, (1974). The concept of direct iodination of benzene in the gas phase over the zeolite 13X has been suggested in Japanese Patent Publication No. 82/77631 in the absence of any oxidizing agent.

Ishida and Chono in Japanese Kokai No. 59/219241 have suggested a technique for oxyiodinating benzene over very acidic zeolite catalyst having a silica to alumina ($SiO_2:Al_2O_3$) ratio of greater than 10. In this technique benzene is reacted with iodine in the presence of oxygen to produce iodinated benzene. According to this disclosure approximately 96% of the benzene which is converted is converted to iodinated form. However, the remaining benzene is oxidized to carbon dioxide and other combustion products resulting in the loss of valuable starting material.

4. Other Information

Subsequent to the present invention, Paparatto and Saetti disclosed in European Patent Applications Nos. 181,790 and 183,579 techniques for oxyiodination of benzene over zeolite catalysts. European Patent Application No. 181,790 suggests the use of ZSM-5 and ZSM-11 type zeolites which have been exchanged prior to use with the least one bivalent or trivalent cation. According to this disclosure the utilization of these zeolites in the acid or alkaline form results in a rapid decrease in catalytic activity in relatively few hours.

European Patent Application No. 183,579 suggests the utilization of X type or Y type of zeolite in nonacid form. According to No. 183,579 the X or Y zeolites have to be used in the form exchanged with monovalent, bivalent or trivalent cations and in particular with alkaline or rare earth cations. The techniques of Nos. 181,790 and 183,579 prepare the monoiodobenzene in selectivities in excess of 90% and only minor amounts of the diiodobenzene compounds.

Accordingly, a need exists for a process which can iodinate benzene at high conversions with substantially no oxidation of the benzene ring.

Further need exists for a process which selectively produces paradiiodobenzene with substantially no oxidation of the benzene ring.

Another need exists for a process which iodinates naphthalene preferentially at the 2-position with minimum formation of oxidation products.

A further need exists for a process which produces diiodonaphthalenes with minimal oxidation of the naphthalene starting material.

5. Related Applications

The United States application Ser. No. 912,806 filed Sept. 29, 1986 and entitled Processes for Preparing Iodinated Aromatic Compounds discloses the oxidative iodination of aromatic compounds over zeolite catalysts. U.S. application Ser. No. 029,898, filed Mar. 25, 1987 discloses the use of oxidation catalysts in combination with a zeolite or other basic site containing catalyst to iodinate aromatic compounds.

The disclosures of the above-referenced applications are herein incorporated by reference.

BRIEF DESCRIPTION OF THE INVENTION

Accordingly, one object of the present invention is to provide a process for the iodination of hydrocarbon aromatic compounds.

Another objective of the present invention is to provide a process for the iodination of benzene which does not utilize the strong oxidizing agents of the prior art.

Another objective of the present invention is to provide a process for the oxidative iodination of benzene in the absence of oxidative degradation.

Yet a further object comprises a process for the oxidative iodination of benzene over non-zeolite catalysts.

A further objective comprises a process for the oxidative iodination of naphthalene in the substantial absence of oxidation of the naphthalene.

These and other objects which will become apparent from the following disclosure have been achieved by the following inventions:

(1) reacting iodine with benzene in the presence of a source of molecular oxygen over a solid catalyst which contains alkaline or alkaline earth cations;

(2) reacting naphthalene with iodine in the presence of a source of molecular oxygen over a solid catalyst that possesses aklaline or alkaline earth cations.

DESCRIPTION OF THE PREFERRED EMBODIMENTS

Benzene

The oxidative iodination of benzene may be performed over essentially any solid catalyst which possesses alkaline or alkaline earth cations. If the catalyst is supported on a porous support the pore sizes should be about 6 Å or larger, which is the apparent size of the benzene ring. If the benzene cannot enter into the pores but is limited to reactions occuring on the external surface of the catalysts only, the degree of conversion to the iodinated form will be low. The catalysts of this invention contain alkaline or alkaline earth cations. These cations are provided by compounds containing an alkaline or alkaline earth element. Examples include magnesium oxide on silica, calcium aluminate, magnesium aluminate, sodium iodide on alumina, potassium chloride on silica, calcium chloride on silica-alumina, barium hydroxide on alumina, and the like. Lithium compounds may also be used. The counterion to the alkaline or alkaline earth cation is not critical.

A catalyst containing the alkaline or alkaline earth cation may be supported or unsupported. Essentially any conventional catalytic support may be employed, but it is preferred to employ catalyst supports which do not contain acid sites. It has been found that the presence of acidic sites in the catalyst system causes excessive oxidation of the benzene ring to carbon dioxide and other oxidation products. Catalyst supports which are suitable include silica, alumina, titania, silica-alumina, or combinations thereof. Catalyst supports containing acid sites may be utilized, preferably after neutralizing the acid sites.

In the present process the iodine source is not critical and can include iodine as $I_2$, hydriodic acid in gaseous form, alkyl iodides, preferably $C_1$-$C_6$ alkyl iodides, or mixtures thereof. The degree of iodination is largely controlled by the mole ratio of iodine to benzene. When only a monoiodinated product is desired the ratio of iodine to benzene should be 2 moles of benzene for every mole of iodine. When polyiodinated products are desired, larger ratios of iodine to benzene would be utilized. By controlling the mole ratio of iodine to benzene it is possible to selectively produce mono, di or triiodobenzenes. When producing polyiodinated benzene over the catalyst one will usually obtain a mixture of isomers.

Catalysts which contain a mixture of acid and basic sites may be used in the present invention but will result in increased combustion of the benzene and are not preferred. When a catalyst contains both acid and basic sites it is preferred to ion exchange the catalyst with an alkali or alkaline earth metal to remove or neutralize the acid sites thereby decreasing the oxidation of the benzene and improving the selectivity of the catalyst for the desired iodinated benzenes.

The total surface area of the catalyst is not critical. Obviously, the more active sites on the catalyst the greater the productivity of the process per volume of catalyst employed. The catalyst may be prpared in powder form and then combined with a binder or support to produce a shaped catalyst. Alternatively, the active catalyst may be impregnated onto an inert support form aqueous or non-aqueous solutions. The particular catalyst shape is a matter of choice and convenience.

It is also possible to utilize the catalyst in powder form, especially when the reaction is to be conducted in a fluidized bed or in the liquid phase wherein the catalyst would be suspended in the liquid reactant.

The temperature at which the reaction is conducted is not critical and is largely determined by whether one desireds to conduct the process in the liquid or vapor phase. The temperature need only be high enough to ensure that the catalyst is active and should be below the temperature at which the benzene would undergo excessive combustion during the process. Temperatures from 100° to 500° C. may be utilized, with temperatures of from 250 to 400 being preferred, with the most preferred range being from 200° to 350° C. In general, the utilization of lower temperatures tends to favor the selectivity of the process to paradiiodobenzene although the catalyst activity as measured by percent conversion decreases with decreasing temperature. However, unreacted benzene or incompletely reacted benzene may be recycled to the reaction to increase the overall conversion to the desired level.

The pressure at which the process is conducted is not critical and can range from subatmospheric to superatmospheric. The utilization of elevated pressures in the gas phase process may be preferred so as to minimize equipment size. In general, pressures from atmospheric to 600 psig have proven satisfactory.

The molecular oxygen can be introduced as pure oxygen, air or oxygen diluted with any other inert material such as carbon dioxide or water vapor. Oxygen from any convenient source may be utilized in the present process. The purpose of the oxygen is to regenerate the active site on a catalyst to its active form once the iodination reaction has occurred. Thus the amount of oxygen present during a reaction is not critical. It is preferred that at least ½ mole of oxygen be used for every mole of iodine. The molar ratio of iodine to benzene which is to be reacted is largely determined by whether one desires to produce a monoiodobenzene product or a polyiodobenzene product. Stoichiometrically ½ mole of iodine reacts with 1 mole of benzene to produce the monoiodinated form. Similarly on a stoichiometric basis 1 mole of iodine is required to convert 1 mole of benzene to the diiodinated form. Greater or lesser quantities of iodinating can be utilized as the artisan may desire. The utilization of excess quantities of iodine will result in a product which is contaminated with unreacted iodine. In general, it is desired to run the process to obtain as close to 100% conversion of the iodine as practical so as to simplify the purification steps and the recovery of the unreacted iodine. Suggested mole ratios of benzene to iodine to oxygen are from about 1:0.01:0.01 to about 1:2:3. However other ratios may be utilized as desired. The molar ratio of iodine to benzene is not critical and is largely a matter of choice.

While it is anticipated that the present process would be carried out continuously by the continuous addition of iodine, oxygen and benzene to the reactor, the process can also be carried out as a batch or semibatch process as desired. While it is preferred that the iodination of the benzene with the iodine will be performed simultaneously with the oxidation of the catalyst back to the active form, it is possible to conduct the process utilizing two reactors and circulating the catalyst between them. In the first reactor the iodine and benzene can be introduced to react to form the iodinated benzene. The catalyst could then be cycled to a second reactor where it is contacted with oxygen and returned to the active state and the catalyst then reintroduced into the first reactor to catalyze the iodination of additional benzene. This same effect can be achieved in a single reactor by alternately feeding a mixture of iodine and benzene and then oxygen.

The space velocity in the process is not critical and may be readily selected by the artisan. For vapor-phase operation gas hourly space velocities between 10 and 50,000, preferably between 100 and 20,000 liters per hour of reagents per liter of active catalyst have proven satisfactory.

The catalyst has an extremely long life and degrades only slowly with time. The degradation of the catalyst is believed to be caused by the decomposition of very small quantities of benzene which deposit small quantities of carbon on the active sites thereby degrading catalyst activity. When the reaction conditions are selected such that no benzene is decomposed, the life of the catalyst is essentially indefinite. However, should the catalyst become deactivated, reactivation of simple. An excellent regeneration technique comprises passing oxygen over the catalyst for several hours at a temperature above 400° C., although higher or lower temperatures have proven equally satisfactory. The temperature need only be high enough so as to ensure combustion of he carbon deposit on the catalyst. When pure oxygen is employed lower temperatures can be utilized, while when air is employed temperatures of about 400° C. are proven satisfactory.

The iodinated benzene compounds produced by the process of this invention are useful as intermediates. Monoiodobenzene can be hydrolyzed to phenol which can be used for resins according to methods well known in the art. Diiodobenzene can be aminolyzed to diamines useful for preparing polyamide resins according to known techniques.

Naphthalene and Condensed Ring Aromatics

It is well known that naphthalene and other condensed ring aromatics are more susceptible to oxidation than benzene. Thus, it was quite surprising to find that naphthalene and condensed ring aromatics could be oxyiodinated over the present catalysts with substantially no oxidation of the ring structure. Still more surprising was the discovery that the oxyiodination reaction favors the 2-position on the naphthalene ring. Prior conventional liquid iodination techniques for iodinating naphthalene, such as the utilization of nitric acid or other strong oxidants has preferentially produced iodination in the 1-position; greater than 99% of the product was iodinated in the 1 or $\alpha$ position. The present process preferentially iodinates the two-position with minimum iodination at the 2 or $\beta$ position being at least 50%. This ability to selectively iodinate the 2-position is important since it is the 2.6-naphthalene dicarboxylate, a ($\beta$-$\beta$ dicarboxylate) which is of principle commercial interest.

In order to successfully iodinate naphthalene and other condensed ring aromatics, it is preferred that the catalyst be substantially free of acid sites. If the catalyst or its support contains substantial quantities of acid sites the combustion of the naphthalene and other condensed ring aromatics will be excessive. The presence of a small number of acid sites may be tolerated if the degree oxidation of the condensed ring aromatic is acceptable. The degree of oxidation which is acceptable will vary from artisan to artisan depending upon processing economics and the like. In the preferred embodiment the degree of oxidation is the minimum practical.

The catalysts of this invention contain alkaline or alkaline earth cations on an inert support. These cations are provided by compounds containing an alkaline or alkaline earth element. Suitable cations include lithium, sodium, potassium, rubidium, cesium, magnesium, calcium, strontium, and barium. The counterion employed is not critical. Suitable anions include sulfate, hydroxide, carbonate, iodide, bromide, chloride, fluoride, nitrate, etc. We speculate that under oxyiodination conditions the anion is eventually replaced by iodide. These catalysts may be supported or unsupported as desired. If the catalyst is to be in porous form, it is preferred that the pore size be greater than about 6 Å which is the apparent size of the naphthalene molecule. When using other condensed ring aromatics the pore size is chosen depending upon the apparent size of the condensed ring aromatic being iodinated.

The reaction conditions are chosen such that the naphthalene or other condensed ring aromatic is a liquid or gas under the reaction conditions. Thus, the temperature and pressure conditions are selected such that the starting material is either in the liquid or vapor state or both. It is possible to conduct the process under reaction conditions wherein the naphthalene or other condensed ring aromatic is constantly vaporizing and condensing, i.e., at or near its boiling point. The particular temperatures employed may range from a low of 100° C. to a high of 400° C. More preferably from about 150° to 400° C. and most preferably from about 200° to 350° C. In general, the lower temperatures favor the production of the 2.6-isomer over the 2.7-isomer. The use of the lower temperatures does result in reduced catalytic activity and reduced conversion.

The total surface area of the catalyst is not critical, but the greater the surface area and the greater the number of active sites, the greater the productivity of the process per unit volume of catalyst employed. The catalyst may be utilized in a supported or unsupported state or may be admixed with a binder and extruded into any convenient shape. Suitable binders include alumina, silica, clays and the like to form large granules of extruded shapes or may be utilized in the form of fine powders. The particular shape form of the catalyst is a matter of individual choice. The catalyst may also be impregnated onto an inert support from aqueous or nonaqueous solutions. The preferred form of the catalyst is a porous form wherein the pores are greater than about 6 Å in size. When utilizing a fluidized bed one generally will utilize a smaller prticle catalyst size than when utilizing a fixed bed. When the process is conducted in the liquid phase, the catalyst may be suspended in the liquid phase in the form of fine particles or the liquid may be passed over and/or through a bed of the catalyst, the particular technique being a matter of individual preference.

The molecular oxygen can be introduced as pure oxygen, air oxygen diluted with any other inert material, such as water or carbon dioxide. The purpose of the oxygen is to regenerate the active site of the catalyst to its active form once the iodination reaction has occurred. Thus, the amount of oxygen present during the reaction is not critical, but, it is preferred that at least ½ mole of oxygen be used permole of iodine. The molar ratio of iodine to naphthalene or other condensed ring aromatic which is to be reacted is largely determined by whether one desires to produce a monoiodinated product or a polyiodinated product. Stoichiometrically, ½ mole of iodine reacts with 1 mole of naphthalene to produce the monoiodinated form. Similarly, on a stoichiometric basis 1 mole of iodine is required to convert 1 mole of naphthalene or other condensed ring aromatic to the diiodinated form. Greater or lesser quantities of iodine can be utilized as the artisan may desire. The utilization of excess quantities of iodine may result in a product which is contaminated with unreacted iodine. In general, it is desired to operate the process to obtain as close to 100% conversion of the iodine as practical so as to simplify the purification steps and the recovery of any unreacted iodine. Suggested mole ratios of naphthalene to iodine to oxygen are from about 1:0.05:0.05 to about 1:2:3. Similar ratios of condensed ring aromatic to iodine to oxygen are utilized when utilizing other condensed ring aromatics. The molar ratio of iodine to naphthalene or other condensed ring aromatic is not dance with known techniques. 2.6-Diiodonaphthalene can be aminolyzed to the corresponding diamine which is useful in the preparation of condensation polymers in accordance with known technology.

The following examples are presented to illustrate the present inventions but are not intended in any way to limit the scope of the invention which is defined by the appended claims.

| Ex. No. | Temp. °C. | $C_6H_6$ mmol min$^{-1}$ | $I_2$ mmol min$^{-1}$ | $O_2$ mmol min$^{-1}$ | Catalyst (50 cc) | Products (mole %) | | | wt % $I_2$ |
|---|---|---|---|---|---|---|---|---|---|
| | | | | | | $C_6H_6$ | $C_6H_5I$ | $C_6H_4I_2$ | |
| 1 | 325 | 5.6 | 0.1 | 5.0 | $Al_2O_3$ | 100.0 | 0.00 | 0.00 | 5.5 |
| 2 | 325 | 5.6 | 0.1 | 5.0 | $SiO_2$ | 100.0 | 0.00 | 0.00 | 5.5 |
| 3 | 325 | 5.6 | 0.1 | 5.0 | 30% MgO—$SiO_2$ | 98.2 | 1.78 | 0.00 | 2.7 |
| 4 | 325 | 5.6 | 0.1 | 5.0 | 30% CaO—$Al_2O_3$ | 97.3 | 2.60 | 0.07 | 1.4 |
| 5 | 325 | 5.6 | 1.5 | 5.0 | 10% KI—$Al_2O_3$ | 83.7 | 13.6 | 2.6 | 30.1 |
| 6 | 325 | 5.6 | 1.5 | 5.0 | $Al_2O_3$ | 100.0 | 0.00 | 0.00 | 46.6 |

| Ex. No. | Temp. °C. | $C_{10}H_8$ mmol min$^{-1}$ | $I_2$ mmol min$^{-1}$ | $O_2$ mmol min$^{-1}$ | Catalyst (50 cc) | Products (mole %) | | |
|---|---|---|---|---|---|---|---|---|
| | | | | | | $C_{10}H_8$ | $C_{10}H_7I$ | $C_{10}H_6I_2$ |
| 7 | 225 | 3.0 | 1.5 | 3.0 | 10% KF—$Al_2O_3$ | 93.5 | 5.7 | 0.7 |
| 8 | 225 | 3.0 | 1.5 | 3.0 | 10% KCl—$Al_2O_3$ | 83.0 | 10.9 | 6.1 |
| 9 | 250 | 3.0 | 1.5 | 3.0 | 10% NaCl—$Al_2O_3$ | 78.3 | 13.4 | 8.3 |
| 10 | 250 | 3.0 | 1.5 | 3.0 | 5% $CaCl_2$—$Al_2O_3$ | 76.4 | 14.4 | 9.0 |
| 11 | 300 | 3.0 | 1.5 | 3.0 | 10% KCl—$Al_2O_3$ | 46.2 | 40.4 | 13.4 | critical. Product which is not under iodinated may be recovered and recycled to the reaction to obtain the desired degree of iodinatin.

The space velocity of the process is not critical and may be readily selected by the artisan. Gas hourly space velocities between 10 and 50,000, preferably between 1000 and 20,000 liters per hour of reactants per liter of active catalyst have proven satisfactory.

The source of iodine utilized in the present process is not critical and can include iodine, hydriodic acid in gaseous form or alkyl iodides, especially lower alkyl iodides. Furthermore, mixtures of these iodine sources can also be used.

As condensed ring aromatics which can be utilized in the present process, essentially any condensed ring aromatic may be utilized including anthracene and the like. The reaction conditions utilized with higher condensed ring aromatics are substantially the same as those utilized with naphthalene. When utilizing higher condensed ring aromatics, it may be necessary to adjust process conditions so that the reaction will occur in either the liquid, gas phase or both phases which may require somewhat higher minimum temperatures than is required for naphthalene or may suggest the utilization of subatmospheric pressures.

While it is anticipated that the process would be carried out continuously, batch or semi-batch processing may be practical as well. While it is preferred that the iodination of the condensed ring aromatics would proceed simultaneously with the oxidation of the catalyst back to active form, it is possible to conduct the reaction wherein the catalyst is contacted separately with the oxygen as described above for benzene.

In addition to benzene, naphthalene and anthracene, other unsubstituted aromatic compounds may be iodinated by the present process including pyridines, benzopyridine, thiophenes such as thiophene, benzothiophene, and the like.

The iodinated naphthalene compounds produced by the process of this invention are useful as intermediates. The 2-iodonaphthalene can be hydrolyzed to 2-hydroxynaphthalene which can be utilized for dyes in accor- Obviously, numerous modifications and variations of the present invention are possible in light of the above teachings. It is therefore to be understood that within the scope of the appended claims, the invention may be practiced otherwise than as specifically described herein.

We claim:

1. A process for mono- or di-iodinating an aromatic compound selected from the group consisting of benene, naphthalene, anthracene, pyridine, benzopyridine, thiophene and benzothiophene, which comprises reacting iodine with the aromatic compound in the presence of oxygen at a temperature between 100°–500° C. over a solid iodinating catalyst containing alkaline or alkaline earth cations.

2. The process of claim 1, wherein said solid catalyst contains cations selected from the group consisting of magnesium, calcium, lithium, sodium, and potassium.

3. The process of claim 1 wherein said aromatic compound is benzene.

4. The process of claim 1 wherein said aromatic compound is naphthalene.

5. The process of claim 1, wherein the reaction temperature is between 250° and 400° C.

6. The process of claim 1, wherein
   (a) the source of oxygen is air and
   (b) the oxygen to iodine molar ratio is equal to or higher than the stoichiometric ratio.

7. The process of claim 1, wherein the mole ratios of aromatic compound to iodine to oxygen ranges from about 1:0.01:0.01 to about 1:2:3.

8. The process of claim 1, wherein the process is conducted at a space velocity of 10 to 50,000 liters per hour of reactants per liter of catalyst.

9. The process of claim 8, wherein said space velocity is between about 100 and 20,000 liters per hour of reactants per liter of catalyst.

10. The process of claim 1, wherein said iodinating catalyst does not contain acid sites.

11. The process of claim 1, wherein said catalyst is selected from the group consisting of silica, alumina, titania, silica-alumina and combinations thereof.

12. The process of claim 1, wherein said iodine is provided by a source of iodine selected from the group consisting of elemental iodine, hydroiodic acid and alkyl iodides.

13. The process of claim 1, wherein said molecular oxygen is reacted as pure oxygen, air or oxygen diluted with an inert material.

* * * * *